United States Patent
Schall

(10) Patent No.: US 9,125,658 B2
(45) Date of Patent: *Sep. 8, 2015

(54) METHOD AND DEVICE FOR TISSUE FUSION OR COAGULATION BY TISSUE RESISTANCE-DEPENDENT VOLTAGE-CONTROLLED ELECTRICAL ACTION

(75) Inventor: Heiko Schall, Nuertingen (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 631 days.

This patent is subject to a terminal disclaimer.

(21) Appl. No.: 13/459,296

(22) Filed: Apr. 30, 2012

(65) Prior Publication Data

US 2012/0283730 A1    Nov. 8, 2012

(30) Foreign Application Priority Data

May 3, 2011  (EP) .................................... 11164643

(51) Int. Cl.
*A61B 18/12* (2006.01)
*A61B 18/00* (2006.01)

(52) U.S. Cl.
CPC .... *A61B 18/1206* (2013.01); *A61B 2018/00642* (2013.01); *A61B 2018/00767* (2013.01); *A61B 2018/00875* (2013.01); *A61B 2018/00892* (2013.01)

(58) Field of Classification Search
CPC ................ A61B 18/1492; A61B 2018/00702; A61B 2018/00875; A61B 18/14; A61B 2018/00589; A61B 2018/00791; A61B 2018/00595; A61B 2018/0063; A61B 2018/00827; A61B 2018/00619; A61B 2018/126

USPC ....................................................... 606/40, 50
See application file for complete search history.

(56) References Cited

U.S. PATENT DOCUMENTS

| | | | | |
|---|---|---|---|---|
| 4,860,745 A | * | 8/1989 | Farin et al. ....................... | 606/40 |
| 5,720,744 A | * | 2/1998 | Eggleston et al. .............. | 606/40 |
| 2003/0158551 A1 | | 8/2003 | Paton et al. | |
| 2010/0179534 A1 | | 7/2010 | Podhajsky et al. | |

FOREIGN PATENT DOCUMENTS

| | | |
|---|---|---|
| CN | 1233944 A | 11/1999 |
| CN | 1367666 A | 9/2002 |
| CN | 1525839 A | 9/2004 |
| CN | 101056592 A | 10/2007 |
| EP | 1 862 137 A1 | 12/2007 |
| EP | 2 221 017 A1 | 8/2010 |
| JP | 8-196543 A | 8/1996 |
| JP | 2005-517498 A | 6/2005 |
| JP | 2007-195973 | 8/2007 |
| JP | 2007-319684 A | 12/2007 |

(Continued)

*Primary Examiner* — Rex R Holmes
(74) *Attorney, Agent, or Firm* — Dickstein Shapiro LLP

(57) ABSTRACT

In the method suitable for tissue fusion or coagulation after the commencement of treatment of the tissue, i.e., after completion of a first phase, a second phase is commenced, during which the biological tissue is treated with moderate energy for a certain specified process time. The specification of a functional relationship between the tissue resistance and the output voltage of a supplying source enables the process in phase II to not fall below a minimum treatment time, avoiding premature drying-out of the tissue. A sufficient and reliable bonding of the participating proteins in a moist milieu is reached.

11 Claims, 2 Drawing Sheets

(56) References Cited

FOREIGN PATENT DOCUMENTS

| JP | 2010-194319 A | 9/2010 |
| JP | 2012-529317 | 11/2012 |
| WO | WO 99/65406 A1 | 12/1999 |
| WO | WO 2010/142438 A2 | 12/2010 |

* cited by examiner

METHOD AND DEVICE FOR TISSUE FUSION OR COAGULATION BY TISSUE RESISTANCE-DEPENDENT VOLTAGE-CONTROLLED ELECTRICAL ACTION

RELATED APPLICATION

This application claims priority to European patent application EP 11 164 643.6, filed on May 3, 2011, which is hereby incorporated by reference in its entirety.

TECHNICAL FIELD

Embodiments of the invention relate to a method for tissue fusion or coagulation by at least one electrode that introduces a current into the tissue to be treated.

BACKGROUND

Tissue fusion or coagulation by an electrode that introduces current locally into tissue and/or tissue fluid, is known from, for example, EP 1 862 137 A1.

In the course of introducing current into the tissue, effects arise in the vicinity of the electrode that lead to a change in tissue impedance. At the start of the effect, the tissue has an initial impedance that falls to a lower value shortly after current starts to flow, designated as "phase I". After a period of time, the tissue impedance rises again, designated as "phase II". The tissue impedance in Phase II generally reaches values that lie markedly above the initial impedance. The rise in impedance then flattens out and may reach a stable end value, referred to as "phase III".

The length in time of phases I and II and the slope of the fall and rise in the impedance determine the quality of the surgical result attained.

The system according to EP 1 862 137 A1 therefore attempts to bring the change in tissue impedance over time into line with a target curve. For this purpose, the system compares, on an ongoing basis, the actual tissue impedance value measured in a suitable manner to the target value that applies for the particular point in time. If a deviation is found, then a counter-measure is implemented (for example, an increase or decrease in the energy introduced into the tissue). The control technology approach that forms the basis for this technique, however, can reach its limits if control deviations occur. These may have led to an irreversible change in tissue structure, as is characteristic for the treatment of biological tissue through e.g., protein denaturation.

A robust and reliable method for the performance of tissue fusion or coagulation, in particular vessel anastomosis, is therefore desired. A device that enables this method is also similarly sought.

SUMMARY

The method in accordance with embodiments of the invention is based on the introduction of a current into a biological tissue by way of an electrode, as well as the discharge of the current by way of a counter-electrode. Biological tissue between the two electrodes develops an electrical tissue resistance. Different phases (i.e., phase I, II and III) in the time course of tissue resistance are seen in the period of introduction of current.

The electrical source used to supply the electrode is controlled according to the process. The tissue resistance recorded between the electrode and counter-electrode in at least one of the phases, desirably in phase II, is used as the reference variable. The magnitude of the measured resistance, at least in phase II, is desirably used to regulate the voltage of the source. A change in the voltage of the source can be achieved in circuit technology by corresponding voltage control of the source, for example on the basis of a specified characteristic. The resistance-dependent voltage control of the source is desirably performed during phase II. The change in tissue impedance over time during phase II can therefore be set to a desired behavior. In particular, it is possible to prevent the tissue from drying out too rapidly and thus prevent an unacceptable reduction in the duration of phase II due to an energy input that is too high. In other words, phase II can be carried out in a specified process time. This is conducive to process reliability and ensures good tissue fusion.

It can be ensured that the sequential control for performance of phase II with a timer leads to a desired surgical result of consistent quality. In particular, the regulation of the source voltage as a function of the measured tissue resistance during phase II avoids effects being achieved as a result of premature introduction of too much energy into the tissue that cannot be reversed through a subsequent reduction in the energy input. The proposed closed-loop or open-loop control strategy is therefore particularly expedient for the regulation of the partly irreversible and thus largely non-linear processes in phase II.

A device for carrying out the method in accordance with the embodiments of the invention generally comprises at least one unit to provide electrical power, this unit having an electrical source. The device further includes an instrument connected to the unit with at least one electrode. The electrode is used to introduce the electrical current into the tissue. A control module records the resistance of the tissue and correspondingly controls the voltage of the source. A voltage that is dependent on tissue resistance can be used from phase I. It is, however, also possible to use a fixed voltage or a voltage of the source that is dependent on time.

Such a device also desirably contains an instrument recognition mechanism. The instrument recognition mechanism enables the specification of individual parameters with which the method works with in phase II. Such parameters are, for example, an open-circuit voltage $u_0$, a reference current $i_0$ and/or a characteristic exponent N. The characteristic, on the basis of which the voltage $u_a$ delivered by the source is specified as a function of the tissue resistance $R_a$, can be specified according to the relationship:

$$u_a = u_0 - u_0 \left( \frac{R_a \cdot i_0}{u_0} \right)^N$$

For instrument recognition, code plugs or other storage mechanisms such as a storage mechanism provided on the instrument or any other suitable mechanism can be provided, enabling at least one of the above parameters to be selected for the instrument. In this way, the same process times T2 can be achieved for phase II for different instruments. This enables a high quality of tissue fusion, tissue coagulation and vessel anastomosis to be achieved, and also increases the reliability of treatment, since the surgeon becomes accustomed to a standard effect time of the instrument on the tissue and adjusts to it.

The aforementioned instruments can be monopolar instruments, but are desirably bipolar instruments, such as vessel clamps, the two clamping limbs of which can be formed as the electrode and counter-electrode. Such vessel clamps are used for long-term vessel sealing. A device of this type clamps a vessel and seals it by bonding to one another of opposing tissue walls pressed against each other. Moreover, such an instrument can contain a knife to cut through the sealed vessel.

Monopolar instruments used within the scope of the embodiments of the invention can, for example, have electrodes with a plate or spherical shape, a loop shape or other shape. The counter-electrode does not participate here in the surgical effect; it is attached, for example, as a neutral electrode to the patient.

BRIEF DESCRIPTION OF THE DRAWINGS

Hereinafter, exemplary embodiments of the invention are explained in greater detail with reference to drawings, in which.

DETAILED DESCRIPTION

Figure 1:
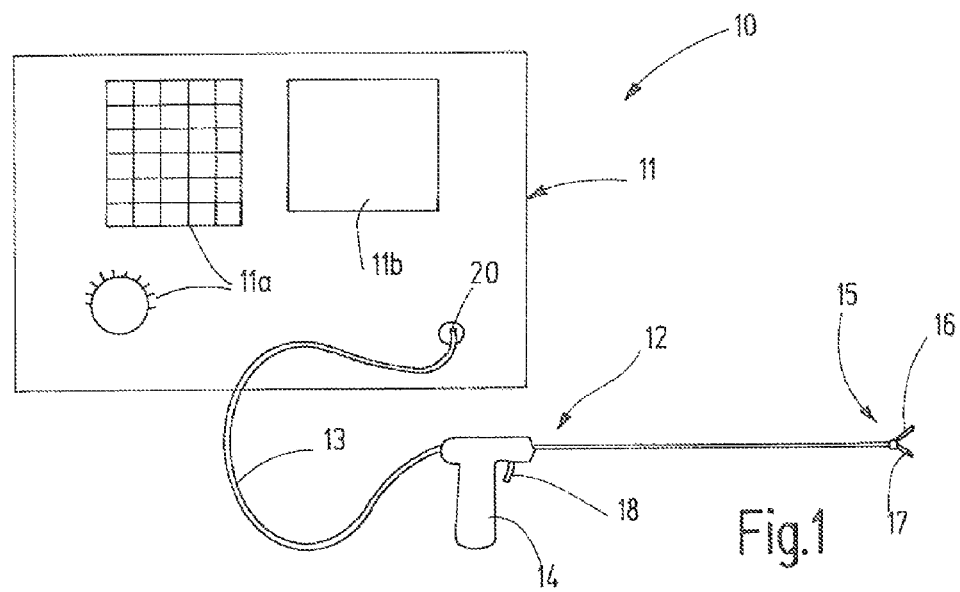
FIG. 1 shows a schematic representation of a device for vessel anastomosis.

FIG. 1 shows a device 10 that represents an example of different devices suitable for tissue coagulation. The device 10 comprises a unit 11 for supplying and operating a surgical instrument 12. The instrument 12 is connected via a line 13 to the unit 11. The instrument 12 is provided with voltage from the unit 11 via the line 13. The unit 11 has different operating elements 11a and/or one or more display elements 11b, for example one or more display devices.

The instrument 12 in the present embodiment is a bipolar vessel clamp with a handle 14 and a tool 15. The latter comprises an electrode 16 and a counter-electrode 17, of which at least one, in this embodiment both, is mounted so they can be moved. The electrode 16 and counter-electrode 17 can be moved towards and away from one another by the actuation of a hand lever 18. Further elements, for example knives to separate vessels, switches or the like can be provided.

It is noted that the instrument 12 does not necessarily have to be a bipolar instrument, as shown in FIG. 1. Monopolar instruments that have just one electrode can also be used. The counter-electrode is then, for example, a neutral electrode to be secured to the patient over a large area where possible.

Figure 2:
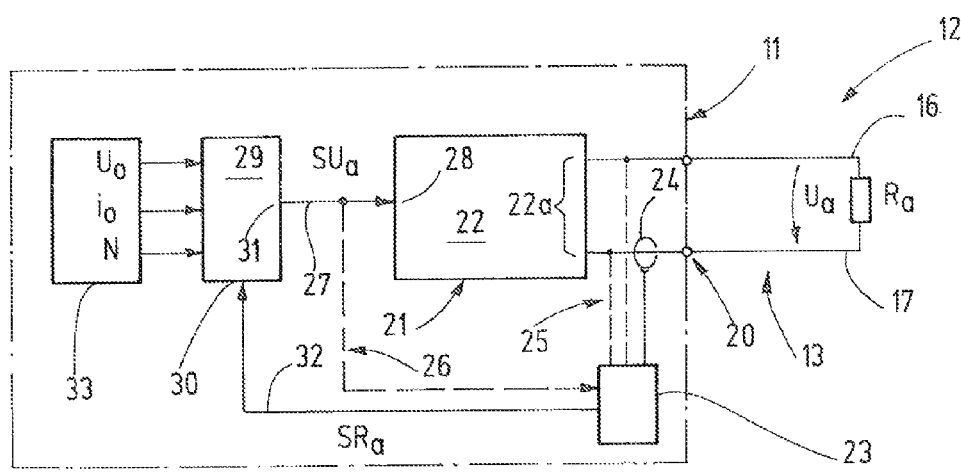
FIG. 2 shows a block diagram of the device according to FIG. 1.
Figure 5:
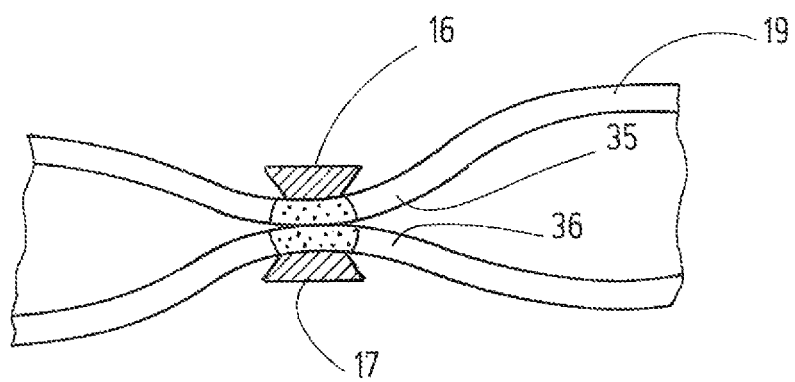
FIG. 5 is a schematic representation of parts of a longitudinal section through a vessel during vessel sealing.

The basic electrical structure of the device 10 is shown in FIG. 2. A resistance $R_a$ symbolizes the impedance, which in the simplest case is the ohmic resistance of the tissue 19 gripped between the electrodes 16, 17. Such tissue 19 can, for example, be a blood vessel, as shown in FIG. 5. The electrodes 16, 17 are shown in FIG. 2 solely as lines reduced to their electrical function. They are connected to the unit 11 via the line 13 and a plug connector 20.

The instrument 12 is supplied with electrical power by a source 21, which is a DC or AC voltage source, desirably a high frequency (HF) generator 22. The source 21 provides a high-frequency AC voltage in the range of, for example, several hundred kilohertz and if necessary several hundred volts, and also over a thousand volts for cutting, contact-free coagulation or ablating applications. The HF generator 22 delivers the HF power to the electrodes 16, 17.

An impedance sensor 23 may be arranged in one of the corresponding lines, for example in the line leading to the counter-electrode 17; the sensor 23 generates a signal that, depending on the embodiment, characterizes the complex impedance, the value of the impedance, the blind component of the impedance or the ohmic tissue resistance $R_a$ of the biological tissue 19 gripped between the electrode 16 and the counter-electrode 17.

To record the tissue impedance, the impedance sensor 23 can be connected to a current sensor 24, which characterizes a current flowing through the tissue resistance $R_a$ at the impedance sensor 23. The impedance sensor 23 cannot establish the tissue resistance $R_a$ directly because of the varying output voltage $u_a$. In the present embodiment, the impedance sensor 23 receives a further signal that characterizes the voltage $u_a$. This signal can be directly tapped from the lines leading to the electrode 16 and the counter-electrode 17. A corresponding signal path 25 is shown by the dashed line in FIG. 2.

Alternatively, if the source 21 has a sufficiently low internal resistance, then a signal $su_a$ corresponding to the output voltage $u_a$ can be transmitted via an alternative signal path 26 to the impedance sensor 23. The signal path 26 is connected to a signal path 27, which in this embodiment of the HF generator 22 delivers the signal $su_a$ as a control signal to an input 28 of the source 21. The signal $su_a$ at the input 28 determines the magnitude of the output voltage $u_a$ at the output 22a of the HF generator 22.

The unit 11 contains a characteristics block 29 with an input 30 and an output 31, from which the signal path 27 emanates. The characteristics block 29 converts the impedance signal $SR_a$ received from the impedance sensor 23 via a signal path 32 into an output voltage signal $su_a$. The characteristics block 29 realizes the following equation:

$$su_a = u_0 - u_0 \left( \frac{SR_a \cdot i_0}{u_0} \right)^N$$

Because of the negligible internal resistance of the source 21, the output voltage $u_a$ corresponds to the output voltage signal $su_a$. Moreover, the tissue impedance $R_a$ corresponds to the tissue impedance signal $SR_a$. Consequently:

$$u_a = u_0 - u_0 \left( \frac{R_a \cdot i_0}{u_0} \right)^N.$$

Figure 3:
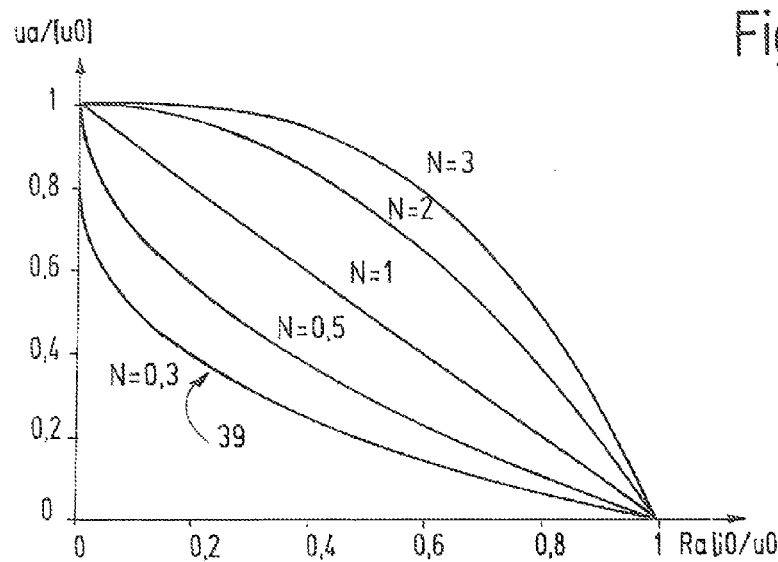
FIG. 3 shows a diagram to illustrate the method of voltage control with the device according to FIGS. 1 and 2.

The characteristics specified by the characteristics block 29 are shown in FIG. 3. They depend on the magnitude of the characteristics exponent N and on a reference current $i_0$ and the open-circuit voltage $u_0$. These variables are delivered by a block 33 that transfers the variables $u_0$, $i_0$ and N, which are constant for the particular operation, to the characteristics block 29.

In a simple embodiment, the block 33 can specify the three variables $u_0$, $i_0$ and N in a fixed manner. It is, however, also possible for these variables to be made accessible, at least to very experienced personnel, so that they can be adjusted. In a preferred embodiment, the block 33 contains an instrument recognition module (not shown in any further detail). The recognition module can communicate, for example, with a storage device provided on the instrument 12, for example an EPROM or the like. Line connections, not shown, or the existing line 13 can be used for this purpose. It is also possible to provide an RFID recognition mechanism, or the like. Alternatively, the plug 20 can be in the form of a code plug that characterizes the design, type, size or purpose for which the instrument 12 is used. The block 33 can be set up to recognize this plug. The block 33 can, to that extent, perform an assignment of various recognized instruments or instrument types to the appropriate open-circuit voltage $u_0$, the appropriate reference current $i_0$ and/or the appropriate characteristics exponent N.

The impedance sensor 23, the characteristics block 29 and the block 33 can be realized by specific circuits or by software. In particular, they can be programs or parts of programs of one or more microcontrollers.

The device 10 functions as follows:

It is presumed that a surgeon wishes to seal a blood vessel 19 with the instrument 12. The surgeon therefore grips the blood vessel 19 between the electrode 16 and the counter-electrode 17 and actuates the hand lever 18 to press opposing sections 35, 35 of the wall of the blood vessel 19 against one another, as shown in FIG. 5. A suitable measure such as e.g., the actuation of the hand lever 18 or the actuation of a further switch which may be e.g.; provided on the handle 14, then activates the delivery of power by the unit 11.

Figure 4:
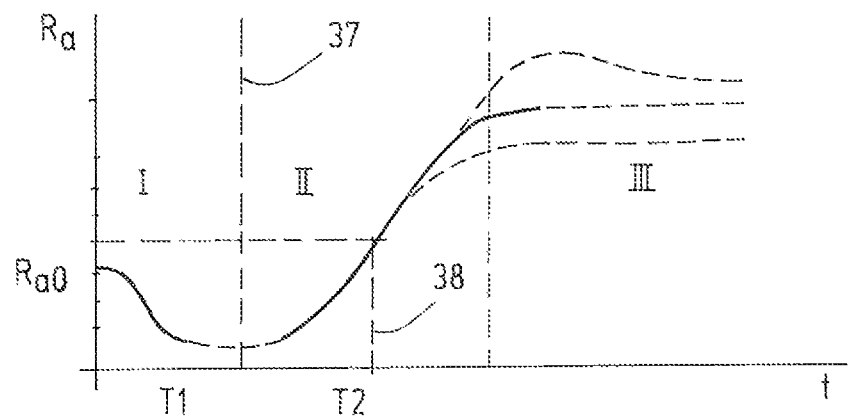
FIG. 4 is a diagram to illustrate the variation in tissue resistance over time.

As long as no current is flowing to the blood vessel 19, it has an initial impedance of, for example, 20 ohms or a similar value. This is shown in FIG. 4 in time interval T1. The tissue impedance $R_a$ is shown logarithmically on the vertical scale. Once current is flowing through the blood vessel 19, the tissue impedance $R_a$ falls relatively rapidly, for example, individual cells open and current paths filled with electrolytes are formed. In this first phase I, it is possible to work according to a suitable fixed mode, for example, with a constant voltage $u_a$, constant power, constant current or according to other criteria. This may be fixed in advance. It is also possible for the unit 11 to be configured such that the individual modes for phase I are selectable or adjustable, for example, by the operating elements. It is also possible to include an instrument recognition mechanism, which, for example, works together with a storage mechanism provided in the instrument 12, and which accordingly sets the operating mode of the HF generator 22/source 21.

The progress of the process is monitored during phase I so that the start of phase II can be recognized. Monitoring can, for example, be carried out by monitoring the flowing current or by monitoring other physical variables such as the phase angle of an electrical variable, the current, the voltage between the electrode 16 and the counter-electrode 17 or the tissue impedance $R_a$. The time curve in FIG. 4 shows that it is possible to use the first renewed rise in tissue resistance $R_a$ (after it has reached a minimum) as an indication of the starting of phase II. This is indicated in FIG. 4 by a vertical dashed line 37. It is, however, also possible to set other limit values or threshold values. For example, the start of phase II can also be defined as that point in time at which tissue resistance $R_a$ is reached again for the first time and which lies markedly above the tissue resistance $R_{a0}$ measured at the start of phase I. This is indicated in FIG. 4 by a second vertical dashed line 38.

Regardless of how the starting point of phase II is defined, at the start of phase II the unit 11 switches to a phase II operating mode that differs, or can differ, from the previous operating mode. In phase II, the output voltage $u_a$ of the unit 11 corresponds to the characteristic specified by the characteristics block 29 as a function of the measured tissue resistance $R_a$. In FIG. 3, a typical characteristic 39 is marked out of many possible characteristics. It is possible, for example, with an instrument 11 suitable for this characteristic, for the output voltage $u_a$ to be correspondingly specified to the measured tissue resistance $R_a$. As can be seen, the unit 11 seen from the instrument 12 has a non-linear negative internal resistance (for N≠0).

The HF generator 22 itself may actually have a low positive internal resistance or an internal resistance of practically zero. However, the output voltage $u_a$ tracks the measured tissue resistance $R_a$ such that a desirably non-linear negative internal resistance of the supplying source 21 results. The sum of the negative internal resistance thus formed is desirably lower than the tissue resistance $R_a$.

As a result of the specified characteristics, a decreasing current $i_a$ flowing through the tissue leads to a decreasing generator voltage and vice versa. In this way, the more rapidly the tissue resistance $R_a$ rises, the more slowly the voltage $u_a$ rises and thus the input of energy into the tissue. This leads in phase II to a specified process time T2 shown in FIG. 4. The process time T2 can thus be kept largely constant for larger or smaller vessels and independently of physiological differences between individual patients, thus leading to a high treatment reliability and treatment quality.

The end of phase II is reached once the specified process time T2 has elapsed. The coagulation process can then be continued in phase III or stopped according to suitable requirements.

In the method suitable for tissue fusion or coagulation after the start of treatment of the tissue, i.e., after phase I is over, phase II commences during which the biological tissue is treated with moderate energy input for a certain specified process time. By the specification of a functional relationship between the tissue resistance $R_a$ and the output voltage $u_a$ of a supplying source 21, it can be ensured that the process in phase II does not fall below a minimum treatment period so that premature drying-out of the tissue is avoided. A sufficient and reliable bonding of the participating proteins in a moist milieu is attained.

What is claimed is:

1. A method of tissue fusion or coagulation by at least one electrode connected to an electrical source that is also connected to a counter-electrode, said method comprising:
   determining, on an ongoing basis, an electrical tissue resistance that results between the electrode and the counter-electrode; and
   controlling an output voltage delivered by the electrical source based on the determined tissue resistance between the electrode and counter-electrode,
   wherein a functional relationship is specified for controlling the output voltage as a function of tissue resistance, the functional relationship being given by:

$$u_a = u_0 - u_0 \left( \frac{R_a \cdot i_0}{u_0} \right)^N$$

where N is a characteristics exponent and is a positive or negative number that is not zero, $u_a$ is the output voltage, $u_0$ is the open-circuit voltage, $i_0$ is the reference current, and $R_a$ is the tissue resistance.

2. The method according to claim 1, wherein N is a whole number.

3. The method according to claim 1, wherein at least one of the parameters is specified by an instrument recognition mechanism.

4. The method according to claim 1, wherein the electrical source delivers a high-frequency AC voltage.

5. A device for tissue fusion or coagulation by high-frequency alternating current, said device comprising:
- an electrical source having an output for delivering, at least temporarily, a high-frequency AC voltage with a negative internal resistance,
- at least one electrode connected to the output and configured to be brought into interaction with a biological tissue to bring about a surgical effect,
- at least one counter-electrode is connected to the output and configured to be brought into electrical connection with the biological tissue.

6. The device according to claim 5, further comprising:
- an impedance sensor for an ongoing determination of electrical tissue resistance developing between the electrode and the counter-electrode, the impedance sensor generating an impedance signal characterizing the electrical resistance, and
- a characteristics block connected to a control input of the source and providing it with an output voltage signal on the basis of the impedance signal provided by the impedance sensor, said output voltage signal being available at an the input of the source and determining the magnitude of the voltage delivered by the electrical source,
- wherein the characteristics block embodies a functional relationship between the output voltage signal and the impedance signal.

7. The device according to claim 6, wherein the functional relationship contains parameters selected from an open-circuit voltage, a reference current and/or a characteristics exponent, the functional relationship being given by the relationship $$u_a = u_0 - u_0 \left( \frac{R_a \cdot i_0}{u_0} \right)^N$$

wherein N is the characteristics exponent and is a positive or negative number that is not zero, $u_a$ is the output voltage, $u_0$ is the open-circuit voltage, $i_0$ is the reference current, and $R_a$ is the tissue resistance.

8. The device according to claim 7, characterized in that at least one of the parameters is specified by a device for instrument recognition.

9. The device according to claim 5, wherein the electrical source is a high-frequency AC voltage source.

10. The device according to claim 5, wherein an impedance sensor continuously measures the electrical resistance.

11. The device according to claim 5, wherein an impedance sensor measures the electrical resistance at discrete time intervals.

* * * * *